United States Patent
Vergara

Patent Number: 5,928,134
Date of Patent: Jul. 27, 1999

[54] EXTERNAL DEVICE FOR ELUDING MASCULINE IMPOTENCE

[76] Inventor: Roberto Jose Romero Vergara, Turina 10-1o., 47006 Valladolid, Spain

[21] Appl. No.: 08/789,956

[22] Filed: Jan. 30, 1997

[30] Foreign Application Priority Data

Jan. 30, 1996 [ES] Spain ..................................... 9600211

[51] Int. Cl.⁶ ........................................................ A61F 5/00
[52] U.S. Cl. ................................................. 600/38; 600/39
[58] Field of Search ..................................... 128/844, 842, 128/918, 885; 604/347–353; 600/37, 38, 39

[56] References Cited

U.S. PATENT DOCUMENTS

| | | | |
|---|---|---|---|
| 1,013,924 | 1/1912 | Butterlich | 600/39 |
| 4,653,484 | 3/1987 | Cannon | 600/39 |
| 4,953,542 | 9/1990 | Tsirjulnikov | 600/39 |
| 5,065,744 | 11/1991 | Zusmanovsky | 600/39 |

*Primary Examiner*—Michael A. Brown
*Attorney, Agent, or Firm*—Kolisch Hartwell Dickinson McCormack & Heuser

[57] ABSTRACT

An external device for eluding masculine impotence, comprising: (A) SUPPORT, with a rigid core and a softer lining, it lies along the penis, to which it communicates its rigidity, since both are enveloped in a preservative. To avoid tautness, rubbing and pinching, the inner side of the preservative is previously wetted with an aqueous type lubricant. (B) FASTENER, made of rigid material, is attached to said support by means of two hinges, thus maintaining the support in its proper place despite the effort exerted during its use. (C) TIE, made of soft, flexible material, maintains the fastener well tightened to the body by pulling from it from the front and rear. It is useful for coitus performance when the erection is nonexistent or insufficient in intensity or duration.

20 Claims, 1 Drawing Sheet

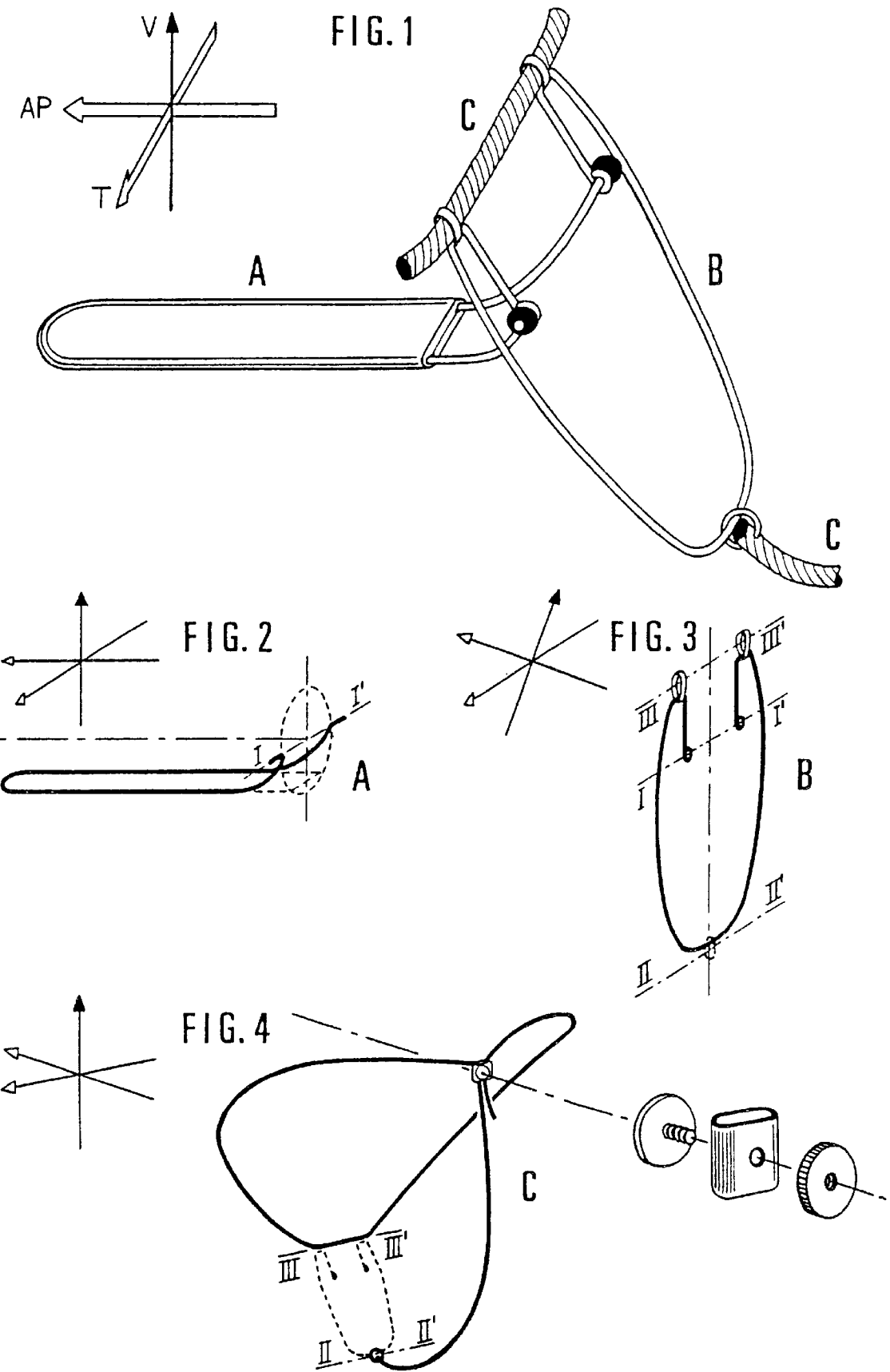

EXTERNAL DEVICE FOR ELUDING MASCULINE IMPOTENCE

TECHNICAL FIELD

This invention refers to a mechanical apparatus relating to sexology. It is not a prosthesis, since the device does not replace any part of the body. Nor is it an orthopaedic article, since it is intended to correct not a physical deformity but a dysfunction. And neither is it merely an erotic toy.

THE PROBLEM

Masculine impotence is the male's inability to achieve and maintain an erection to a sufficient degree for full coitus performance.

The rigidity in a normal erection is caused by the swelling of the cavernous bodies: two erectile tubes contained in the penis which are attached to the pubic bone by the penis' suspensory ligament. In order to maintain an erection, a 40 to 60 milliliter/minute blood flow is necessary. The length of an erect penis normally varies from 8 to 16 centimeters; its circumference perimeter, from 8 to 11 centimeters. However, impotence is a matter of rigidity, not size: the penetrating force in the vagina under normal circumstances is approximately 5 newtons (i.e. half a kilo), an exercise which is possible only if the penis acquires a sufficient rigidity; simply increasing the size is not enough.

The majority of men are said to suffer an erectile disfunction at some time in their lives. However, a severe condition arises on reaching a 20% failure index. The causes of impotence can be: a) Of a psychic or mental source, such as life traumas, sense of guilt, apprehension of failure, etc., and generally any emotionally stressing condition, including a subconscious one. b) Of a physical or organic source, such as certain ailments, medicines, alcoholism, drug addiction, neurological, hormonal and vascular problems (blood irrigation), and sequelae from traumatisms, malformations, etc., namely deriving from anatomic and metabolic alterations. Causes of a psychic and organic nature can be simultaneously present in one same individual.

Such a variety of causes reveals that the erection mechanism is an extremely complex and vulnerable one. According to the most optimistic statistics, severe impotence affects more than 7% of men; according to the most pessimistic, it affects up to 10–11% of the male population. For example, there are 1.5 million impotent men in Spain and 10 million in the US. In any case, impotence becomes more frequent with age, progressing toward a definite condition: before the age of 35, it is rarely present; as from 60, in one man in every five; at 70, almost 30% of men are impotent; at 75, more than half; at 80 years of age, three in every four.

Organic causes currently account for 70% of impotences. It is worthwhile noting that in the past decades statistics attributed a larger number of cases to psychic causes than at present, a fact that may be explained by the continuous advances experienced in medical diagnosis. (For example, a useful criteria—which is nowadays instrumentally detectable—for detecting deficiencies of a physical origin is the absence or low quality of the involuntary erections which should take place in the course of night sleep. This is also diagnosed by techniques as sophisticated as contrast arteriography).

STATE OF THE ART

In order to assess the comparative advantages of the present invention, as described hereinafter, a brief knowledge of the state of the art is necessary.

At present (1995), the list of remedies—either real or fictitious—against impotence is enormous. This being an issue of general interest, it is easy to obtain data from informative books and from wide circulation newspapers and magazines. Going through the causes of impotence, as previously indicated, it follows that the remedies may act on the mind, on the metabolism or on the anatomy, namely on three levels: psychic (or psychosomatic), biochemical and mechanical.

1. Psychotherapeutic treatments—These treatments preach recovery through the force of the mind, thereby seemingly restricting their action to causes of a psychic nature. However, there are experts who also attempt addressing causes of an organic nature in this way. These methods, being highly prone to incredulity and superstition, may either be set apart from official medical practices (Oriental philosophies, certain forms of charlatanry) or else be recognized by them (psychoanalysis, hypnosis). They require a great deal of confidence and patience, and usually involve long, slow-healing treatments.

2. Invigorating products—Many have been used for centuries, ingested under various forms. Those prepared from cantharis (the cantharis, mistakenly referred to as the "Spanish fly", is a coleopteron insect with the shape of an elongated beetle) are reputedly as efficient as they are dangerous, containing a toxic matter which causes irritation to the urinary conducts and produce priapism which may lead to death if administered in sufficiently high dose. Neither is yohimbine (an alkaloid extracted from the bark of the yohimbe tree found in Cameroon) exempt from risk, since it is a powerful hypertensor. The wood of the miura-puama tree, from Brazil, is used for aphrodisiac infusions. Ginseng root is actually a beneficial tonic for the overall organism which is however not miraculous; although free of contraindications, it is extremely expensive. Other products of a vegetal origin (crushed plant parts) are used in single or mixed form, generally by way of infusions. Rhinoceros horn, one of the most exotic aphrodisiacs and highly in demand in certain Arab countries, has placed this animal species on the verge of extinction. Also, and according to popular belief, certain seafoods, such as oysters and many other products, are effective; they are rich in vitamins and trace elements, and are particularly useful in deficiency conditions deriving from illness or poor nutrition. Substances such as prostaglandin (present in certain organs, particularly in the prostate) and papaverine (an opium alkaloid) injected in the penis are appropriate in the event of, for example, neurological problems (damaged nerves) caused by spine damage; if applied incorrectly, they may cause severe disorders to the penis, a strict medical control being therefore necessary. Testosterone (a testicle hormone) is used for impotences of a hormonal nature, although it has an adverse effect on prostate cancer and is occasionally administered rashly and without control (as in the case of certain preparations sold freely in sex shops).

3. Acupuncture, digitopuncture and special massage techniques—These are means of mechanically stimulating nerve centers and organs throughout the body. Applied by experts, they are used against numerous ailments, one of them being impotence.

4. Repair surgery—Certain vascular disorders are corrected through surgery by repairing injuries in arteries which impair normal blood irrigation. The patient's health is a conditioning factor.

5. Implanted prostheses—These are devices inserted in the penis through surgery, wherein they remain permanently lodged. Earlier models were semirigid, constant erection prostheses consisting in silicone rods with a resilient core similar to a spring which prevented the appearance of a normally limp condition, this being awkward for the user in the event of undressing in public, i.e. in gym shower rooms, during medical examination, etc. Current semirigid, more advanced prostheses comprise two parallel silicone rods which can be bent by a simple external operation to simulate erection or limpness. Inflatable prostheses are even more sophisticated, providing not only rigidity but also a very realistic increase in volume. They consist of a pair of tubes which may be inflated at will by liquid pumped along respective small tubes via a small hand-operated pump located inside the testicle bag. The liquid container is fixed inside the abdominal cavity, next to the bladder. Another inflatable model is available which substitutes said container and pump by a single element located entirely outside the abdominal cavity. The main drawback affecting protheses are surgery and high cost, inflatable units being extremely expensive.

6. External constricting devices—The earliest such device consists in a ring which, being adjusted to the base of the penis, grasps it firmly in order to prolong the erection. However, a previous erection is necessary, albeit poor and brief, and the device is therefore not useful in cases of severe impotence. Vacuum erection apparatuses comprise a tubular chamber at one end of which a hand-operated air suction device is coupled; upon being inserted through the other end, the penis is subject to an external pressure considerably lower than the atmospheric pressure and thus experiences an extra blood afflux and is erected. A rubber ring is then slid to clasp the basis of the penis and thus prevent the blood from escaping upon withdrawal of the vacuum apparatus. These constriction or strangling techniques are always uncomfortable and sometimes painful. Additionally, the rings may be kept in place for a strictly limited period of time in view that blood circulation in the penis is interrupted, the basic principle being precisely that of forcibly checking the blood flow.

7. External non-constricting device—This is the object of our present invention, as described hereunder.

GENERAL DESCRIPTION OF THE INVENTION: BASIC CONDITIONS

A natural erection is a very complex physiological process because of the multiple factors involved (psychic, hormonal/biochemical, neurological, vascular), although it is readily understandable on a local level if restricted to its mechanical aspect: blood flows with sufficient pressure into the cavernous bodies of the penis, swells them and is sufficiently retained therein by a valvular system which impairs its free return to the organism's general circulating system. The penis thus increases in size and becomes hard.

There are techniques which address the issue of impotence at this local level without attacking the roots of the problem. The vacuum apparatus supplants the natural flow of blood. The ring supplants the valvular blood retaining system. The implanted prostheses—and also our invention—totally disregard blood as the "hydraulic fluid" or driving element to produce the erection, their operation being independent from the subject of blood irrigation.

A) First element: the support—This invention basically consists of a purely mechanical rigid element which conveys its rigidity to the penis and is not implanted internally as a prosthesis but is attached externally by the resilient force of a prophylactic which envelops both the penis and the supporting element. Since it is located outside the body, the installation thereof requires no surgery (it may be put on and taken off in one minute) and neither does it alter the penis' structure. This rigid element is closely adapted in a longitudinal direction and is therefore elongate in shape—either rectangular or otherwise—with a length similar to that of a limp penis and wide enough to provide a stable support (some 2 cm). It may be flat or slightly curved in a transverse direction, the concave side being in contact with the penis. For added comfort, it may be lined with foam rubber or some similar lining material (flesh-coloured) on both sides and along the edges. In order to avoid tautness, friction and pinching of the penis, which may be subject to violent movement or even changes in size, the prophylactic must be wetted internally before putting it on, using an aqueous, non oily type lubricant which will not alter the properties of the rubber or harm the skin. This rigid element or SUPPORT is positioned as best as possible against the underside of the penis, where it is perfectly concealed under the prophylactic. There are various ways of adapting the length of the support in each case: by means of an enlargeable support, a sliding cover or simply a selection of interchangeable supports.

B) Second element: the fastener—The support, strictly by itself, would be worthless. Owing to back and forth movement it would be offset from its correct position on the limp penis and would alternatively be pushed backwards and drawn forwards up to the point of becoming altogether separated from the penis and prophylactic; some type of unalterable external fastening to the penis is therefore essential. This fastening may be achieved, for example, by attaching to one of the ends of the support a simple part in the form of a butt designed to transmit the thrust on the pubes, which provides a solid support. However, this attachment would be very precarious since it would hardly neutralize the traction effort alternating with the pushing effort, requiring this part to be permanently pressed against the pubes with the help of a hand, the act of having a hand permanently occupied and under tension being very limiting and uncomfortable. In view of all these reasons, a second element must be added to provide an efficient attachment: the FASTENER, a part made of rigid material onto which the support is attached. This fastener, which may have different shapes, basically consists of two symmetric longitudinal stretches which lean against the right and left zones at the base of the penis; these stretches are joined by a third lower transverse stretch which leans against the perineum or by an upper transverse stretch which leans on the pubes, or by two transverse stretches (upper and lower). The fastener may thus respectively have an upright U shape, an inverted U shape, or an elongate ring shape. It may be totally or partially covered by soft material, and is somewaht cocealed within the pubic hair. The support-fastener attachment comprises two hinges with horizontally oriented rotation axes (so that the penis can move up and down to adapt itself to the various postures) and is furthermore located at an approximately diametrical height in respect to the penis (so that the support will experience no relative movement under the penis, that is, advancing beyond the glans when the angle is lowered or retreating toward the testicles when the angle is raised); likewise, both hinges, via their external pivots, also serve to engage the edge of the prophylactic, which is thus retained and is prevented from sliding out despite the limpness and the action of the lubricant.

C) Third element: the tie—It serves to attach the support both to the front (pubes) and the rear (perineum), holding it firmly in place. It is made of material that is comfortable to the touch. It comprises a flat strap or a round string which pulls the fastener in three directions: two branches going from the pubes towards the hips and a third branch going from the perineum upwards, all three joining in the lumbar area. Thus, its design is identical to that of a "tanga"; the tie, if flesh coloured or transparent, is unobtrusive and hardly visible. An ordinary belt may also be used to engage a clasp at the height of the kidneys and one or two clasps at the front. Not to mention other even less discrete fantasy versions which may extend above the waist. All these ties may be non-extensible or relatively resilient, either throughout their length or in one or several stretches.

DESCRIPTION OF AN EMBODIMENT OF THE INVENTION: A PRACTICAL PROTOTYPE

FIG. 1 shows a prototype 100 constructed according to the principles set forth. The perspective view is based on three orthogonal spatial axes, the names of which refer to the user's body: anterior-posterior axis AP (front-rear), transverse axis T (left-right) and vertical axis V (up-down).

Support (element A, FIG. 2)—Composed of a hard steel spring rod (diameter=2.5 mm) curved 180 degrees in the middle 1 to form an elongate U having parallel elongate members 2, 3 (length=85 mm), width between axes of elongate members 2, 3=17 mm), the ends 4, 5 thereof extending (20 mm more) and being helicoidal and symmetrically curved sinistrorsely 6 and dextrorsely 7 (helix diameter=35 mm); at the end of these helices respective folds 8, 9 form protrusions which function as male hinges embedded in their respective spherical pins 10, 11, having a I–I' precise diametrical rotation axis. The protrusions also are configured to retain the edges of a prophylactic which has been unrolled over the support past the protrusions. The flat part in the support—i.e. the U—is not diaphanous but covered by a fully enveloping lining 12 made of a dense, brown colour foam rubber with an impervious surface; it is therefore soft to the tact and of an increased size (width=20 mm, thickness=5 mm). The lining 12 is retained by virtue of contact adhesive extended over the inner walls.

Fastener (element B, FIG. 3)—Also composed of a steel spring rod (diameter=2.5 mm). It is U-shaped and includes curved arms 13, 14 adapted to lean on both groins (if the arms 13, 14 were straight and somewhat parallel, they would lean on the base of the scrotum, a softer an more sensitive part than the groins). The ends 15, 16 of the U extend and bend symmetrically toward the inside of the U, turning into two straight, parallel stretches 17, 18 ending in respective loops or curls 19, 20; these are the female hinges for the support-fastener hinged joint, fitted with a I–I' rotation axis. Said symmetric ends 15, 16 lie within respective plastic rings or hoops 21, 22 which allow the tie C to pass along axis III–III', parallel to axis I–I' (distance between both axes=25 mm). The length of the U does not vary (90 mm). However, the distance or tolerance between the hinges (35 mm under zero force) may increase or decrease as a result of the design and the resilient material, adapting itself spontaneously to each individual's penis or to each situation. The separation between the hinges and the arms 13, 14 of the U removes the risk of the scrotum being pinched when the support A rotates on the hinges. The steel—both in the support A and in the fastener B—is protected by an epoxy, brown colour lining.

Tie (element C, FIG. 4)—This is an impermeable, very flexible leather string 23 of a round cross section (diameter=5 mm). One of its ends is diametrically perforated by a minuscule round ring 24 with a II–II' central axis; said ring 24 engages the fastener B through the bottom of the U of fastener B, pulling it backwards. The string 23 also pulls the fastener B upwards, in the direction of the hips, from the III–III' axis rings 21, 22. To fasten the tie C, once the correct tension has been adjusted, a kind of press buckle 25 is provided at the height of the lumbar region, shown in an exploded view in the drawing. Screw 26 attaches through sleeve 27 to secure string 23 with nut 28.

Arrangement for use—The complete device, including all its elements together, with a loose buckle 25, is put on like a pair of pants or trousers, taking care to allow first the testicles and then the penis to pass inside the U of the fastener B, the penis laying on the support A. The buckle 25 is fastened once the tie C has been properly tightened. Sufficient lubricant must then be extended over the penis and the support A. The prophylactic is put on in the usual manner, the penis and the support A both remaining inside. In order to prevent it from sliding outwards, the edge of the prophylactic is unfolded until it extends beyond the spherical hinge pins 10, 11 which serve as a retention means. If the prophylactic fails to provide sufficient support, it must either be replaced or an additional prophylactic placed on top. This is an important aspect.

Lubricants—The only suitable lubricants are hydrosoluble lubricants which harm neither the skin nor the prophylactic's rubber, which do not stain and which are furthermore easily removed by washing. Fortunately, gynecological and urological lubricants are available in the market which provide such features, containing water, glycerine, hydrosoluble polymers and occasional additives such as colouring agents, spermicides such as Nonoxynol-9, bacteriostatical agents such as chlorhexidine gluconate and contact anaesthetics such as tetracaine hydrochloride (these last one are only for medical use, and must thus be discarded). In regard to their physical aspect, they can be gelatinous ointments packed in tubes (e.g. British lubricant K-Y, made by Johnson & Johnson) or viscous liquids packed in jars (e.g. U.S. lubricant Slip Plus, made by Trimensa Pharmaceuticals); the liquids, being less viscous than the ointments, usually provide a bigger sliding property. A gelatinous lubricant may be diluted in water and then shaken thoroughly until perfect homogenization is achieved, reducing its viscosity to the degree desired by the user. When these products are not available, home-made lubricants can be a risky substitute: an improvised lubricant would be metilcellulose paste, a hydrosoluble polymer used as a food additive and as an adhesive for wall paper; at medium concentration (in the order of 1/60), it is surprisingly effective, although a few days after being prepared it becomes useless. Furthermore, it could contain fungicides or other non-specified additives which may prove to be allergenic or irritating.

Improvements—The prototype described is an illustrative though not arbitrary example for the shapes and dimensions. Experience shows that apparently irrelevant details are crucial. Concerning the materials used, in-series production allows for multiple improvements: instead of epoxy-covered carbon steel, stainless steel or quality plastics may be used, alone or fiber reinforced (composite materials), allowing for the fabrication of ergonomical designs; instead of foam rubber, other filling materials may be used which are able to cover the support with a soft, discardable lining enabling the hardness and the volume to be modified at will; instead of the leather string 23, other flexible washable materials such as coloured, transparent, somewhat resilient plastics may be used; the press buckle 25 may be replaced by a simple running noose if the tie C is designed for a single specific size established by the user after using the device for the first time, cutting the new string to suit his own size.

COMPARATIVE ADVANTAGES OF THE INVENTION

The present invention allows it to be used almost universally among the adult masculine population. Its use is restricted only by rare physical limitations—such as specific injuries and malformations or an abnormally small penis—and is conditioned neither by age, general health condition nor other factors which are otherwise crucial in the practical application of many of the other remedies.

The present invention is sufficiently EFFECTIVE to guarantee—in the absence of the above mentioned impediments—the possibility of coital penetration, including cases of total impotence. Obviously, the greater the volume and the turgidity, the greater the resemblance to a natural erection. However, two facts have been confirmed in actual practice; 1) the prophylactic may simulate a certain turgidity over a limp penis because it compresses the penis radially, while at the same time somewhat increasing its length, and 2) the fastener hinges leaning on soft compressible tissue area create the optical illusion that the penis is approximately 1 cm longer than it actually is; these two facts are important in difficult cases wherein the penis is too short and is furthermore affected by total impotence. This guaranteed penetration possibility is not provided by many aphrodisiacs and other remedies and techniques, particularly in the event of severe impotence.

The present invention provides an IMMEDIATE RESPONSE, being easily and rapidly installed and ready to work in less than a minute; it is ideal for inadvertent failures or temporary incapacity conditions caused by medicines, for instance. Other remedies take months to provide the first sign of an improvement.

The present invention is INDEPENDENT from the help provided by third persons. Its use does not call for qualified experts such as psychologists, natural healers, andrological doctors, surgeons, etc. The user has only to read a simple operational leaflet once.

The present invention is INNOCUOUS to the organism. It does not attack the metabolism the way other invigorizing products do. It requires no surgery like implanted prostheses. It does not strangle blood irrigation as in the case of the rings. It does not violate the emotional intimacy of a person in the way certain psychotherapeutical treatments do. It does not worsen a delicate health condition beyond what a natural erection would.

The present invention is COMFORTABLE to use if installed properly and with the necessary lubricant. It causes no discomfort or irritation as other ingested or injected products do, and neither does it produce the grasping feeling provided by the rings. Consequently, it can be used on a permanent basis for an indefinite period of time.

The present invention will probably prove ACCEPTABLE to many ethical and religious creeds, since it does not harm a person's dignity beyond that of a walking stick or a plaster cast, for instance. Concerning the theoretical possibility of conception, the protruding end of the prophylactic can easily be cut off if the user so desires, since the device will work equally well.

The present invention is COMPATIBLE with other cures or techniques applied against impotence. It can therefore be used simultaneously with other treatments which, although more efficient, may cause the user to become impatient because of their slowness or insufficiency.

The present invention is LESS EXPENSIVE than other products if produced in series, because it is quite simple.

Finally, the hypothetical possibility exists that the present invention actually cures psychic impotences caused by the fear of failure; if a person uses the device and thus makes sure that he will not fail, he may actually achieve a natural erection which will however not be hampered by the use of the device.

COMMERCIAL IMPLEMENTATION

This invention requires a series of accessories that are essential, and so a practical form of marketing is suggested herein. This would include a small case or handbag with a zipper, made of leather or similar material, containing the following objects arranged in an orderly fashion: (1) A complete device 100, comprising the three above mentioned components A, B, and C. (2) Two additional supports A, one longer and the other shorter than the standard length already mounted in the device 100, used for a better adaptation to the user in extreme cases. (3) A box of linings 12 for the support A. (4) A box of prophylactics. (5) A small bottle or tube containing hydrosoluble dermic lubricant. (6) Paper handkerchiefs or sealed wet towels for emergency purposes in the event that no washing or drying facility is available. (7) A small operation instructions booklet, including advice on the set's proper preservation, washing and sterilization.

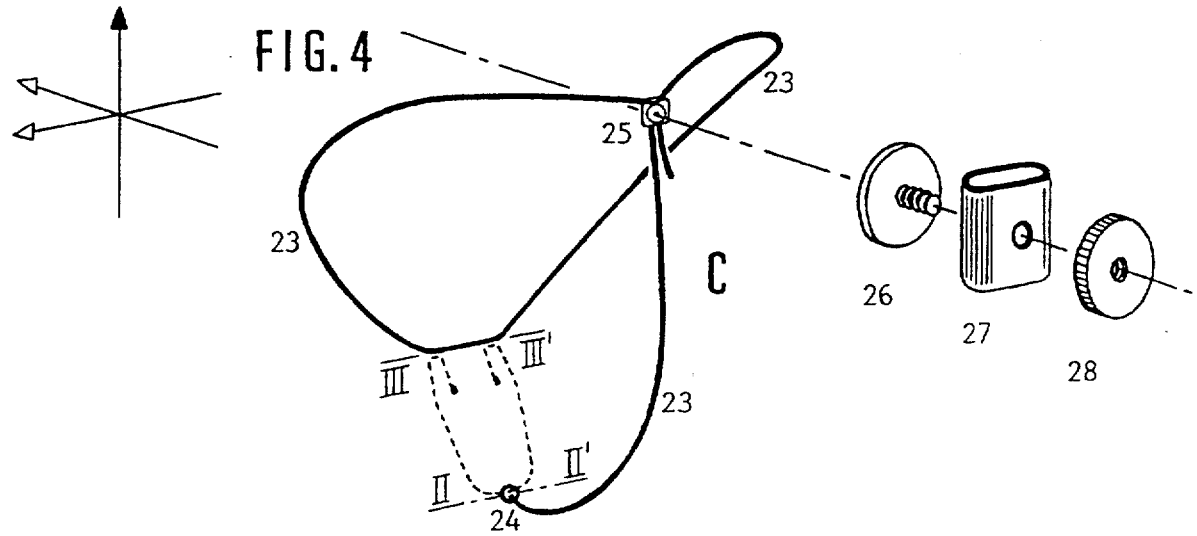

I claim:

1. An external device for eluding masculine impotence, comprising:
   an elongate rigid support which may be lined with a softer lining;
   a prophylactic enveloping the rigid support, and sized to envelop a penis along with the support;
   a U-shaped rigid fastener shaped to settle around genitals and attached to the support by a hinge having a rotation axis that is approximately diametrical in respect to a penis enveloped by the prophylactic; and
   a flexible tie which attaches the fastener to a human by pulling on the fastener from the front (pubes) and rear (perineum) and transmits its force along three branches to a joining point located in the lumbar zone.

2. The device of claim 1 wherein the support further comprises a second elongate member, substantially parallel to the first elongate member.

3. The device of claim 2 wherein a softer lining spans an area between the first and second elongate members.

4. The device of claim 3 wherein the softer lining slides longitudinally along each of the first and second elongate members and is sufficiently rigid such that it can alter the effective length of the support.

5. The device of claim 3 wherein the softer lining is disposable and replaceable by a new lining.

6. The device of claim 1 wherein the support is detachable from the fastener at the hinge.

7. The device of claim 1 wherein said fastener further comprises at least one protrusion configured to engage an edge of the prophylactic such that the prophylactic is retained in a position partially enveloping the support and a penis.

8. The device of claim 1 wherein the fastener further comprises two opposed curved arms joined at a common point, each curved arm being configured to rest against a respective left or right groin region at a base of a penis when the support is pushed toward a torso.

9. The device of claim 1 further comprising a softer lining that slides longitudinally along the support and is sufficiently rigid such that it can alter the effective length of the support.

10. The device of claim 1 wherein the support is detachable from the fastener at an end of the support.

11. The device of claim 1, wherein an inner face of the prophylactic is wetted with a water-soluble lubricant.

12. The device of claim 1, wherein the hinge also serves to retain an edge of the prophylactic relative to the rigid support.

13. The device of claim 1, wherein the flexible tie is a string.

14. The device of claim 1, wherein the flexible tie is a tape.

15. An external device for eluding masculine impotence, comprising:
- an elongate rigid support which may be lined with a softer lining;
- a prophylactic enveloping the rigid support, and sized to envelop a penis along with the support;
- a ring-shaped rigid fastener shaped to settle around genitals and attached to the support by a hinge having a rotation axis that is approximately diametrical in respect to a penis enveloped by the prophylactic; and
- a flexible tie which attaches the fastener to a human by pulling on the fastener from the front (pubes) and rear (perineum) and transmits its force along three branches to a joining point located in the lumbar zone.

16. The device of claim 15, wherein the support further comprises a second elongate member, substantially parallel to the first elongate member.

17. The device of claim 15, wherein said fastener further comprises at least one protrusion configured to engage an edge of the prophylactic such that the prophylactic is retained in a position partially enveloping the support and a penis.

18. The device of claim 15, further comprising a softer lining that slides longitudinally along the support and is sufficiently rigid such that it can alter the effective length of the support.

19. The device of claim 15, wherein the flexible tie is a string.

20. The device of claim 15, wherein the flexible tie is a tape.

* * * * *

UNITED STATES PATENT AND TRADEMARK OFFICE
CERTIFICATE OF CORRECTION

PATENT : 5,928,134

DATED : July 27, 1999

INVENTOR(S) : Roberto Jose Romero Vergara

Page 1 of 5

It is certified that error appears in the above-identified patent and that said Letters Patent is hereby corrected as shown below:

The title page, showing the illustrative figure should be deleted to be replaced with the attached title page.

In the drawings Figs. 1-4, should be deleted to be replaced with the corrected drawing Figs. 1-4, as shown on the attached pages.

Signed and Sealed this

Twenty-sixth Day of December, 2000

*Attest:*

Q. TODD DICKINSON

*Attesting Officer*     *Director of Patents and Trademarks*

United States Patent [19]

Vergara

[11] Patent Number: 5,928,134
[45] Date of Patent: Jul. 27, 1999

[54] EXTERNAL DEVICE FOR ELUDING MASCULINE IMPOTENCE

[76] Inventor: Roberto Jose Romero Vergara, Turina 10-1o., 47006 Valladolid, Spain

[21] Appl. No.: 08/789,956

[22] Filed: Jan. 30, 1997

[30] Foreign Application Priority Data

Jan. 30, 1996 [ES] Spain ..................... 9600211

[51] Int. Cl.⁶ .......................................... A61F 5/00
[52] U.S. Cl. ............................. 600/38; 600/39
[58] Field of Search ................. 128/844, 842, 128/918, 885; 604/347–353; 600/37, 38, 39

[56] References Cited

U.S. PATENT DOCUMENTS

| | | | |
|---|---|---|---|
| 1,013,924 | 1/1912 | Butterlich | 600/39 |
| 4,653,484 | 3/1987 | Cannon | 600/39 |
| 4,953,542 | 9/1990 | Tsirjulnikov | 600/39 |
| 5,065,744 | 11/1991 | Zusmanovsky | 600/39 |

Primary Examiner—Michael A. Brown
Attorney, Agent, or Firm—Kolisch Hartwell Dickinson McCormack & Heuser

[57] ABSTRACT

An external device for eluding masculine impotence, comprising: (A) SUPPORT, with a rigid core and a softer lining, it lies along the penis, to which it communicates its rigidity, since both are enveloped in a preservative. To avoid tautness, rubbing and pinching, the inner side of the preservative is previously wetted with an aqueous type lubricant. (B) FASTENER, made of rigid material, is attached to said support by means of two hinges, thus maintaining the support in its proper place despite the effort exerted during its use. (C) TIE, made of soft, flexible material, maintains the fastener well tightened to the body by pulling from it from the front and rear. It is useful for coitus performance when the erection is nonexistent or insufficient in intensity or duration.

20 Claims, 1 Drawing Sheet

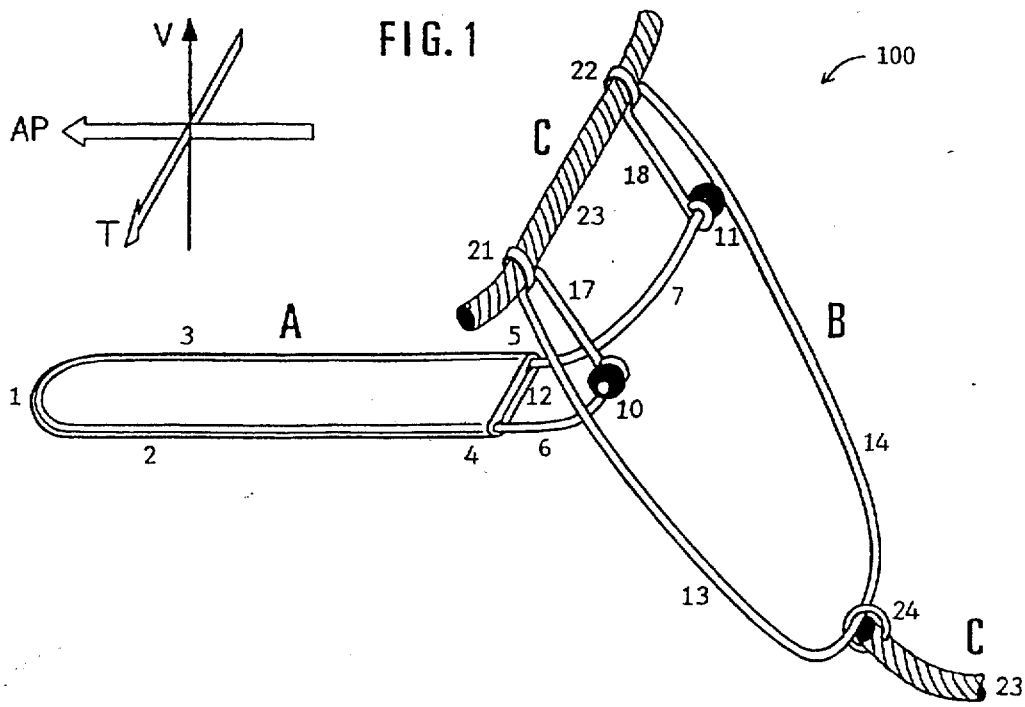

UNITED STATES PATENT AND TRADEMARK OFFICE
CERTIFICATE OF CORRECTION

PATENT NO : 5,928,134
DATED : July 27, 1999
INVENTOR(S): Roberto Jose Romero Vergara It is certified that error appears in the above-identified patent and that said Letters Patent are hereby corrected as shown below:

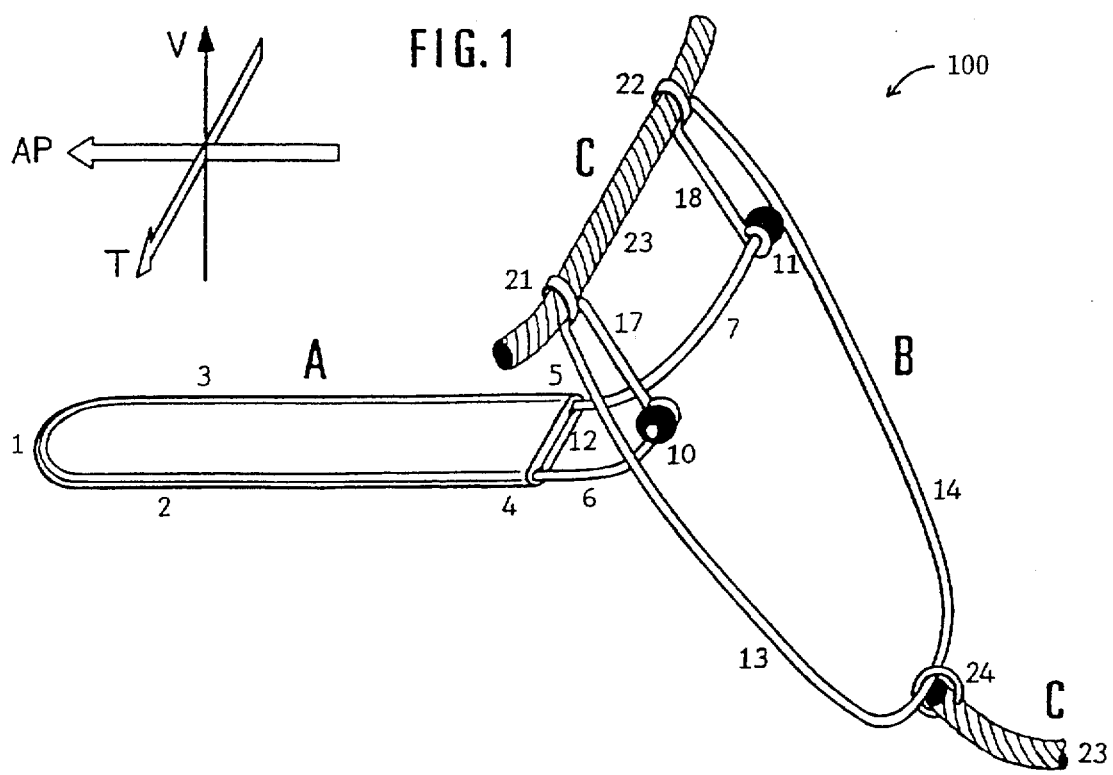

UNITED STATES PATENT AND TRADEMARK OFFICE
CERTIFICATE OF CORRECTION

Page 4 of 5

PATENT NO : 5,928,134
DATED : July 27, 1999
INVENTOR(S): Roberto Jose Romero Vergara It is certified that error appears in the above-identified patent and that said Letters Patent are hereby corrected as shown below:

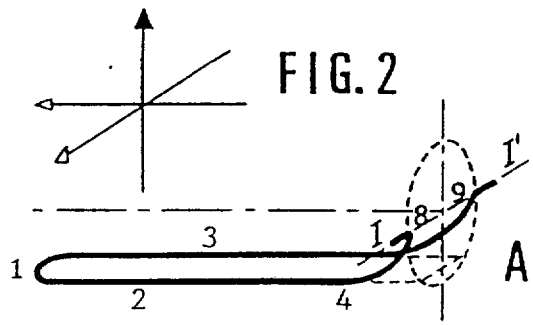
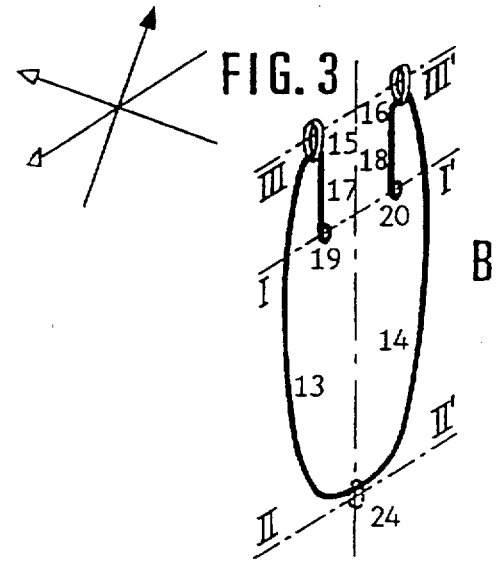

UNITED STATES PATENT AND TRADEMARK OFFICE
CERTIFICATE OF CORRECTION

Page 5 of 5

PATENT NO : 5,928,134
DATED : July 27, 1999
INVENTOR(S): Roberto Jose Romero Vergara It is certified that error appears in the above-identified patent and that said Letters Patent are hereby corrected as shown below: